US006143500A

United States Patent [19]
Nishino

[11] Patent Number: 6,143,500
[45] Date of Patent: Nov. 7, 2000

[54] NUCLEIC ACIDS AND METHODS FOR DETECTING PATHOGENIC *XANTHOMONAS CAMPESTRIS* USING THE SAME

[75] Inventor: Tomoki Nishino, Yokohama, Japan

[73] Assignee: Japan Tobacco, Inc., Tokyo, Japan

[21] Appl. No.: 09/148,801

[22] Filed: Sep. 4, 1998

[30] Foreign Application Priority Data

Sep. 5, 1997 [JP] Japan ..................................... 9-257513

[51] Int. Cl.⁷ .............................. C12Q 1/68; C07H 21/04
[52] U.S. Cl. .......................... 435/6; 536/23.1; 536/24.32; 536/24.33; 435/91.2
[58] Field of Search ................................ 536/24.3, 24.32, 536/23.1; 435/6, 91.2

[56] References Cited

U.S. PATENT DOCUMENTS 5,602,014  2/1997  Mizumura ............................... 435/129

OTHER PUBLICATIONS

Zhang, "The primary structures of the Archaeon *Halobacterium salinarium*", Proc. Natl. Acad. Sci, pp. 8230–8235, Aug. 1996.

Caceres, "Overexpression of the D–alanine Racemase Gene confers Resistance to D–cycloserine in *Mycobacterium smegmatis*", J. of Bacteriology, pp. 5046–5055, Aug. 1997.

Caceres, Genbank Accession No: U70872, Aug. 1997.

Zhang, Genbank Accession No: U62676, 1996.

Mizumura, Genbank Accession No: 135628, Feb., 1997.

Hu, Genbank Accession No: L02630, Apr., 1993.

Maes, "Recognition and Detection in Seed of the Xanthomonas Pathogens that cause cereal leaf streak using rDNA spacer sequences and PCR", Phytopathology, vol. 86, No. 1, pp. 63–69, Jan. 1996.

Vauterin, "Reclassification of Xanthomonas", International J. of Sytematic Bacteriology, vol. 45, No. 3, pp. 472–489, Jul. 1995.

*Primary Examiner*—Lisa B. Arthur
*Assistant Examiner*—Jeanine Enewold
*Attorney, Agent, or Firm*—Birch, Stewart, Birch & Kolasch LLP

[57] ABSTRACT

The present invention is drawn to nucleic acid fragments specific to *Xanthomonas campestris* pathogenic to plants belonging to the family Gramineae, as well as methods for detecting the pathogenic *Xanthomonas campestris* using the same. The nucleic acid fragment of the invention has a nucleotide sequence which is at least 15 consecutive nucleotides of the nucleotide sequence shown in SEQ ID NO:1 or in the complementary chain thereof, or has no less than 15 nucleotides and hybridizes with the nucleic acid having the sequence shown in SEQ ID NO:1 or with the complementary chain thereof under stringent conditions.

16 Claims, 5 Drawing Sheets

NUCLEIC ACIDS AND METHODS FOR DETECTING PATHOGENIC *XANTHOMONAS CAMPESTRIS* USING THE SAME

BACKGROUND OF THE INVENTION

I. Field of the Invention

The present invention relates to novel nucleic acids and methods for detecting *Xanthomonas campestris* pathogenic to plants belonging to the family Gramineae using the same.

II. Description of the Related Art

Bacteria (all bacteria including bacteria pathogenic to plants) are conventionally identified by biochemical assays (examinations for microbiological characteristics) such as metabolizabilities of sugars and organic acids. However, these methods are not quick or simple, but laborious and time-consuming, and require skill. As a method for simply identifying bacteria, a method exploiting the differences in the nucleotide sequences of 16S ribosome RNAs is known. However, by this method, it is difficult to identify the taxonomic group below the species (such as pathovar).

As a method for simply identifying a bacterium belonging to *Xanthomonas campestris*, methods are known in which fatty acids or proteins constituting the bacterial cell are analyzed. However, these methods are not reproducible and it is difficult to distinguish *Xanthomonas campestris* pathovars pathogenic to plants belonging to the family Gramineae from nonpathogenic *Xanthomonas campestris* strains.

Further, to determine whether a *Xanthomonas campestris* strain pathogenic to plants belonging to the family Gramineae exists in natural environment such as in plants, soil or water, it is necessary to apply a sample (plant, soil, river water or the like) obtained from the natural environment on an agar medium, to incubate the agar medium to form a single colony, and to determine whether the bacteria forming the single colony are the pathogenic *Xanthomonas campestris* of interest or not by the above-mentioned conventional method.

SUMMARY OF THE INVENTION

Accordingly, an object of the present invention is to provide means for effectively and quickly detecting *Xanthomonas campestris* pathogenic to plants belonging to the family Gramineae from various samples existing in environment. Another object of the present invention is to provide means for distinguishing or identifying the detected *Xanthomonas campestris* in the level of pathovar or strain.

Through intensive studies a chromosomal DNA region was discovered which is specific to *Xanthomonas campestris* pathogenic to plants belonging to the family Gramineae, which region exists in the chromosomal DNA of pathogenic *Xanthomonas campestris* but does not exist in nonpathogenic *Xanthomonas campestris* and in other bacteria, thereby completing the present invention.

That is, the present invention provides a nucleic acid fragment of which nucleotide sequence is at least 15 consecutive nucleotides in the nucleotide sequence shown in SEQ ID NO:1 or in the complementary chain thereof or which fragment has not less than 15 nucleotides and hybridizes with the nucleic acid having the sequence shown in SEQ ID NO:1 or with the complementary chain thereof under stringent conditions. The present invention also provides a method for detecting a *Xanthomonas campestris* pathogenic to plants belonging to the family Gramineae comprising detecting said nucleic acid fragment according to the present invention. The present invention further provides a probe comprising said nucleic acid fragment according to the present invention and a detectable label attached thereto. The present invention still further provides a method for detection or identification of *Xanthomonas campestris* pathogenic to plants belonging to the family Gramineae comprising digesting a sample nucleic acid with one or more restriction enzymes, separating the obtained fragments by electrophoresis, annealing the separated fragments with said probe according to the present invention, and detecting the probe which hybridized with said fragments. The present invention still further provides a method for detecting a *Xanthomonas campestris* pathogenic to plants belonging to the family Gramineae comprising amplifying a nucleic acid of which nucleotide sequence is shown in SEQ ID NO:1 or complementary thereto, or a fragment thereof, and detecting the amplified nucleic acid.

By the present invention, *Xanthomonas campestris* pathogenic to plants belonging to the family Gramineae may be detected or identified quickly, simply and accurately. Thus, the present invention may be employed for the diagnosis of diseases of the plants belonging to the family Gramineae. Quick diagnosis of the diseases enables therapy at an early stage. Further, by the present invention, it is possible to follow the prevalence of a particular bacterium (i.e., a bacterium pathogenic to plants belonging to the family Gramineae) in a complicated microbiological flora in natural environment or the like. Therefore, population density of a pathogenic bacterium may be determined, which is helpful for the prevention of the disease caused by the bacterium. Further, by the present invention, entering of a bacterium pathogenic to plants belonging to the family Gramineae into a country, which bacterium is attached to seeds or seedlings, may be prevented by detecting the pathogenic bacterium by quarantine. For example, among the *Xanthomonas campestris* pathogenic to plants, which are described in the present specification, those other than *Xanthomonas campestris* pathovar (pv.) *campestris*, *Xanthomonas campestris* pv. *poae*, *Xanthomonas campestris* pv. *hordei* and *Xanthomonas campestris* pv. *translucens* have not been found in Japan. Further, *Xanthomonas campestris* pv. *hordei* and *Xanthomonas campestris* pv. *translucens* have only been reported as pathogenic bacteria for orchard grass and bromegrass which are pasture, and have not been reported as pathogenic bacteria of barley which is an important crop in Japan. Therefore, to quickly detecting and/or identifying *Xanthomonas campestris* pathogenic to plants belonging to the family Gramineae is important in plant quarantine.

BRIEF DESCRIPTION OF THE DRAWINGS

FIG. 5 schematically shows the electrophoretic pattern of the PCR product obtained by subjecting various samples in

DETAILED DESCRIPTION OF THE PREFERRED EMBODIMENTS

To discover a nucleotide sequence specific to *Xanthomonas campestris* pathogenic to plants belonging to the family Gramineae (hereinafter referred to as simply "pathogenic *Xanthomonas campestris*"), a number of restriction fragments of chromosomal DNA of *Xanthomonas campestris* pv. *poae* MB218 (NRR-B-18078) were cloned, and repeatedly subjected chromosomal DNAs of bacteria belonging to the genus Xanthomonas or Pseudomonas to Southern blot hybridization using the cloned chromosomal DNA fragments as probes. As a result, a fragment was dicovered with a size of 1220 bp (hereinafter referred to as "S7 fragment") which may be cut out from the chromosome of *Xanthomonas campestris* pv. *poae* MB218 (NRR-B-18078) by restriction enzyme SalI. *Xanthomonas campestris* pv. *poae* MB218 (NRR-B-18078) has been deposited with NRRL in the U.S. under an accession No. NRR-B-18078 and the strain is freely furnished upon request.

The S7 fragment discovered by the present inventor has homologies to chromosomal DNA regions of pathogenic *Xanthomonas campestris*, that is, *Xanthomonas campestris* pv. *poae, Xanthomonas campestris* pv. *graminis, Xanthomonas campestris* pv. *phlei, Xanthomonas campestris* pv. *arrhenatheri, Xanthomonas campestris* pv. *translucens, Xanthomonas campestris* pv. *undulosa* and *Xanthomonas campestris* pv. *hordei*, but does not have a homology to the chromosomal DNA regions of nonpathogenic bacteria belonging to the genus Xanthomonas and of bacteria belonging to the genus Pseudomonas.

The nucleotide sequence of S7 fragment is shown in SEQ ID NO:1 in the SEQUENCE LISTING. Since S7 fragment is specific to pathogenic *Xanthomonas campestris*, detection of pathogenic *Xanthomonas campestris* may be attained by detecting S7 fragment or a region therein. As is well-known, detection of a nucleic acid having a specific nucleotide sequence can be attained by utilizing hybridization of the nucleic acid to be detected with a nucleic acid complementary thereto. More particularly, S7 fragment or a region therein may be detected by using S7 fragment or a fragment thereof as a probe or a primer for nucleic acid-amplification method such as PCR. Therefore, the present invention provides S7 fragment as well as fragments thereof (either chain of S7 fragment and fragments thereof may be utilized and are within the scope of the present invention). Since the fragments of S7 fragment should be specific to S7 fragment, they should have a size of not less than 15 nucleotides, preferably not less than 20 nucleotides.

Since pathogenic *Xanthomonas campestris* can be detected by detecting the S7 fragment or a region therein, those nucleic acids having a high homology to the S7 fragment or a region therein to such a degree that it can hybridize with the S7 fragment (either chain) or a region therein under stringent conditions may also be used for detecting the S7 fragment or a region therein, and are within the scope of the present invention. The term "stringent conditions" herein mean the hybridization conditions at 60–65° C. in a normal hybridization solution such as 5×Denhardt's solution, 6×SSC,0.5% SDS. Although the nucleic acid according to the present invention may be either DNA or RNA, DNA is preferred in view of high stability.

The S7 fragment may be obtained by digesting the chromosomal DNA of *Xanthomonas campestris* pv. *poae* MB218 (NRR-B-18078) with SalI and by cloning the digested fragments according to a conventional method as concretely described in the Examples hereinbelow described. Alternatively, since the nucleotide sequence of the S7 fragment was determined by the present invention, the S7 fragment may easily be prepared by nucleic acid-amplification method such as PCR using the chromosomal DNA of *Xanthomonas campestris* pv. *poae* MB218 (NRR-B-18078) as a template. Fragments of the S7 fragment may be prepared by chemical synthesis (when the size of the fragment is relatively short) or by nucleic acid-amplification method such as PCR using the chromosomal DNA of *Xanthomonas campestris* pv. *poae* MB218 (NRR-B-18078) or S7 fragment as a template. By these methods, the S7 fragment as well as the fragments thereof according to the present invention may be obtained in isolated form.

As mentioned above, the nucleic acid according to the present invention may be used as a probe for detecting pathogenic *Xanthomonas campestris*. The probe should have a size of not less than 15 nucleotides, preferably not less than 20 nucleotides. The probe may have a size up to the full length of the S7 fragment, that is, 1220 nucleotides.

The probe according to the present invention comprises the nucleic acid according to the present invention and a detectable label attached thereto. The labels which may be used for labelling a nucleic acid to provide a probe are well-known in the art and include radioactive labels, fluorescent labels, biotin label and the like. Kits for labelling nucleic acids to prepare probes are commercially available, and such a commercially available kit may conveniently be used to provide the probe of the present invention.

By annealing a sample DNA and the probe of the present invention, and by checking whether the probe hybridizes with the sample DNA nor not, pathogenic *Xanthomonas campestris* may be detected.

Further, by the so called RFLP (restriction fragment length polymorphism) method using the probe of the present invention, pathogenic *Xanthomonas campestris* may be identified to the level of pathovar. More particularly, a sample DNA is digested with one or more restriction enzymes, and the digested fragments are separated by electrophoresis, followed by annealing the electrophoresed fragments with the probe of the present invention. By so doing, the lengths of the fragments which hybridize with the probe of the present invention differ from pathovar to pathovar (RFLP). Therefore, by carrying out the RFLP analysis using the probe of the present invention, the pathovar of the pathogenic *Xanthomonas campestris* may be identified simply and quickly.

In the RFLP analysis, chromosomal DNA is extracted from the sample bacterium, and the extracted DNA is digested with one or more restriction enzymes. The methods for extracting the chromosomal DNA from bacterial cells are well-known in the art. As the restriction enzymes, EcoRI, EcoRV, SalI and/or PstI may preferably be used, although other restriction enzymes may also be employed.

The digested chromosomal DNA is then separated by electrophoresis such as agarose gel electrophoresis, and the resultant is subjected to Southern hybridization with the probe of the present invention. The electrophoresis and Southern hybridization method are well-known in the art. In cases where agarose gel electrophoresis is employed, the agarose concentration in the agarose gel used in the electrophoresis may be 0.4 to 2.0 wt %, and about 0.7 wt % may be best preferred. The membrane to which the electrophoretic pattern is transferred is not restricted as long as it can surely bind DNAs, and commercially available membranes such as nylon membrane and nitrocellulose membrane may preferably be used. The hybridization condition may be one conventionally used in Southern hybridization, such as at 68° C. for 16 hours in a reaction solution not containing formamide.

Since the nucleotide sequence of the chromosomal DNA region specific to pathogenic *Xanthomonas campestris* was determined by the present invention, pathogenic *Xanthomonas campestris* may be detected by a nucleic acid-amplification method such as PCR which specifically amplifies the above-mentioned region. That is, by subjecting naturally occurring samples (such as plants, soil and river water) to PCR method using the above-mentioned nucleic acid fragments according to the present invention as primers, whether pathogenic *Xanthomonas campestris* exists in the natural environment or not may be determined quickly and simply. How to carry out PCR is well-known in the art and kits and apparatuses therefor are commercially available. The nucleic acid fragments according to the present invention may be used as the primers for such a PCR method.

The above-described nucleic acid fragments according to the present invention may be used as the primers for the nucleic acid-amplification method such as PCR. The size of the primers may preferably be 15 to 50, more preferably 20 to 30 nucleotides. The primer may be any nucleic acid which hybridizes with any region in the S7 fragment (either chain). A preferred example of the forward side primer is the nucleic acid consisting of 25 nucleotides of which nucleotide sequence is shown in SEQ ID NO:2 (this primer is hereinafter referred to as "S7–11 primer"), and a preferred example of the reverse side primer is the nucleic acid consisting of 25 nucleotides of which nucleotide sequence is shown in SEQ ID NO:3 (this primer is hereinafter referred to as "S7–12 primer"), although the primers are not restricted thereto. By carrying out PCR using S7–11 primer and S7–12 primer, and the S7 fragment as a template, a region with a size of 309 bp is amplified. The primers can easily be synthesized chemically. The conditions of each step in PCR varies depending on the size of the region to be amplified, but may be determined by those skilled in the art without difficulty, and a concrete example of PCR is described in the Examples hereinbelow described.

The present invention will now be described in more detail by way of examples thereof. It should be noted that the Examples hereinbelow described are presented for the illustration purpose only and should not be interpreted in any restrictive way.

EXAMPLE 1

Isolation and Sequencing of S7 Fragment and RFLP of Pathogenic *Xanthomonas campestris*

Chromosomal DNA of *Xanthomonas campestris* pv. *poae* MB218 (NRR-B-18078) was extracted by a conventional method and digested with SalI. The obtained fragments were cloned and labeled by using a commercial kit ("DIG DNA Labeling Kit" commercially available from Boehringer Mannheim).

On the other hand, DNAs were extracted from *Xanthomonas campestris* pv. *poae, Xanthomonas campestris* pv. *graminis, Xanthomonas campestris* pv. *phlei, Xanthomonas campestris* pv. *arrhenatheri, Xanthomonas campestris* pv. *translucens, Xanthomonas campestris* pv. *undulosa* and *Xanthomonas campestris* pv. *hordei, Xanthomonas campestris* pv. *campestris*, and *Pseudomonas glumae* and the extracted DNAs were separately digested with EcoRI, EcoRV, SalI and PstI, respectively. Each of the digested DNAs in an amount of 3 $\mu$g was separated by agarose gel electrophoresis using agarose gel with a concentration of 0.7 wt %. Each of the digested product was subjected to Southern hybridization using each of the above-described labeled fragment as a probe. As the blotting membrane, "BIODINE A" commercially available from PALL was used, and for the detection of the signals, "DIG Luminescent Detection Kit for Nucleic Acids" commercially available from Boehringer Mannheim was used. The hybridization reaction was carried out in accordance with the instructions attached to the commercial product "The DIG System User's Guide for Filter Hybridization" commercially available from Boehringer Mannheim, at 68° C. for 16 hours. Among the bacteria mentioned above, *Xanthomonas campestris* pv. campestris alone is nonpathogenic and all of other *Xanthomonas campestris* pathovars are pathogenic to plants belonging to the family Gramineae.

As a result, the S7 fragment used as a probe, which was cut out by the restriction enzyme SalI from the chromosome of *Xanthomonas campestris* pv. *poae* MB218 (NRR-B-18078), hybridized with the DNAs from all of the pathogenic *Xanthomonas campestris*, while it did not hybridize with the DNAs from nonpathogenic *Xanthomonas campestris* and *Pseudomonas glumae*. Thus, S7 fragment which is a fragment specific to pathogenic *Xanthomonas campestris* was obtained. The S7 fragment was sequenced by a commercial DNA sequencer. The determined nucleotide sequence is shown in SEQ ID NO: 1 as mentioned above.

The results of Southern blot analysis obtained by using the S7 fragment as a probe, when the chromosomal DNAs of the bacteria were digested with each of the restriction enzymes, are shown in FIGS. 1–4. FIG. 1 shows the RFLP pattern when the chromosomal DNAs were digested with EcoRI, FIG. 2 shows the RFLP pattern when the chromosomal DNAs were digested with EcoRV, FIG. 3 shows the RFLP pattern when the chromosomal DNAs were digested with SalI, and FIG. 4 shows the RFLP pattern when the chromosomal DNAs were digested with PstI. In FIGS. 11–4, each lane shows the results of the bacteria shown in Table 1 below. As shown in FIGS. 1–4, all of the pathogenic *Xanthomonas campestris* pathovars exhibited different RFLP patterns. These results indicate that pathogenic *Xanthomonas campestris* may be distinguished or identified at a level of pathovar or strain by the RFLP analysis using the S7 fragment as a DNA probe.

| Lane No. | Bacteria |
|---|---|
| 1–13 | *Xanthomonas campestris* pv. *poae* |
| 14 | *Xanthomonas campestris* pv. *phlei* |
| 15–17 | *Xanthomonas campestris* pv. *graminis* |
| 18, 19 | *Xanthomonas campestris* pv. *arrhenatheri* |
| 20–23 | *Xanthomonas campestris* pv. *translucens* |
| 24 | *Xanthomonas campestris* pv. *undulosa* |
| 25 | *Xanthomonas campestris* pv. *hordei* |
| 26 | *Xanthomonas campestris* pv. *campestris* |
| 27 | *Pseudomonas glumae* |

EXAMPLE 2

Detection of Pathogenic *Xanthomonas campestris* pv. *poae* JT-P482 from Environment Suspensions of JT-P482 ($2.0\times10^4$, $2.0\times10^3$ and $2.0\times10^2$ cfu(colony forming unit)/ml), river water, pond water and sterilized distilled water were subjected to PCR using the above-described S7–11 primer and S7–12 primer to examine whether the JT-P482 strain which is pathogenic to annual blue grass that belongs to the family Gramineae and that is a weed in lawn can be specifically detected or not. DNAs were extracted from 0.1 ml of each sample by using "InstaGene (trademark) DNA Purification Matrix" commercially available from Bio-Rad, and recovered by ethanol precipitation. The obtained DNAs were subjected to the PCR employing the conditions shown in Table 2, and 0.01 ml aliquot of the reaction mixture was subjected to electrophoresis in agarose gel with a concentration of 2.0 wt %.

TABLE 2

Conditions of PCR Using S7-11 Primer and S7-12 Primer

Reaction Mixture

| | |
|---|---|
| 10 × LA PCR (trademark) buffer II (Mg$^{2+}$ plus)* | 5 µl |
| DNA Solution | 10–100 ng |
| TaKaRa LA Taq (trademark)* | 0.5 µl |
| S7-11 Primer (20 pmol/µl) | 0.5 µl |
| S7-12 Primer (20 pmol/µl) | 0.5 µl |
| dNTP (each 0.4 mM) | 8 µl |
| Sterilized Distilled Water | Balance to the total volume of 50 µl |

DNA Thermal Cycler

Model 480 (commercially available from Perkin-Elmer Cetus)

PCR

First Step: 94° C. for 1 minute
Second Step: 30 cycles of 98° C. for 20 seconds/68° C. for 1 minute
Third Step: 72° C. for 10 minutes

*LA PCR Kit Ver. 2 commercially available from TAKARA SHUZO

Figure 1:
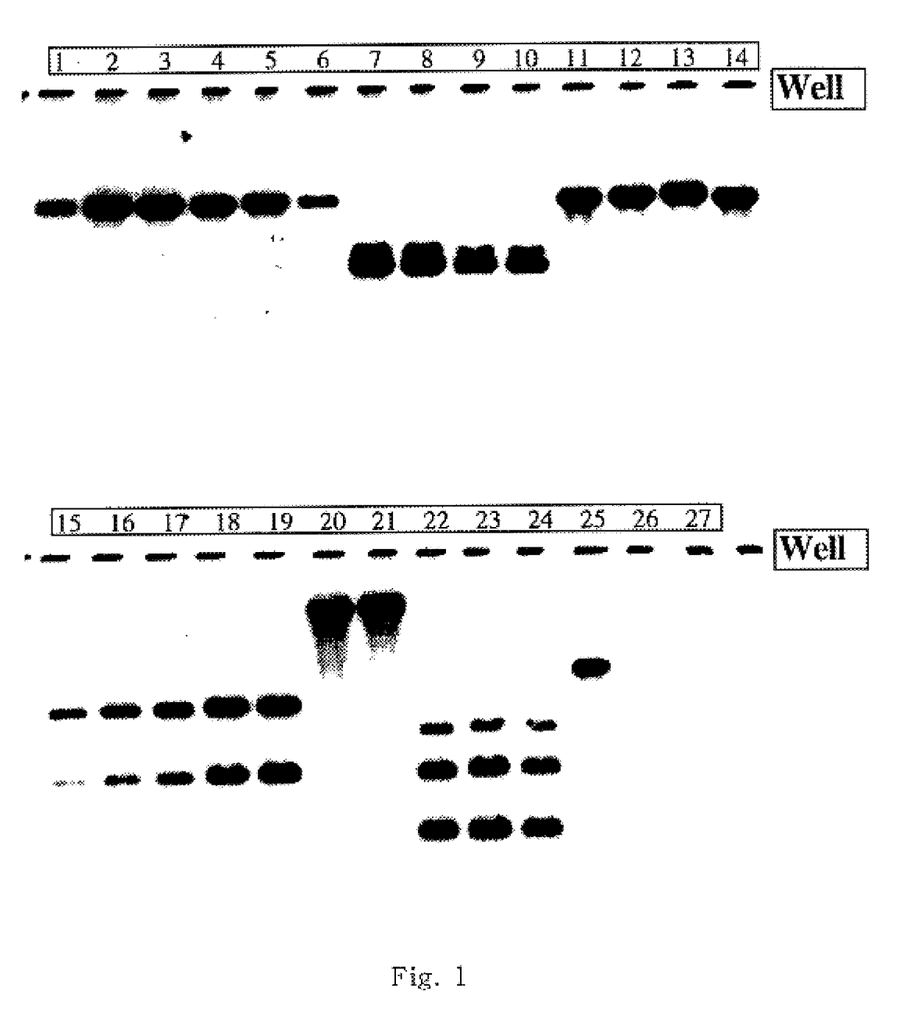
FIG. 1 schematically shows the RFLP pattern obtained by digesting chromosomal DNAs of various bacteria with EcoRI and by subjecting the resultant to Southern hybridization using S7 fragment as a probe.
Figure 2:
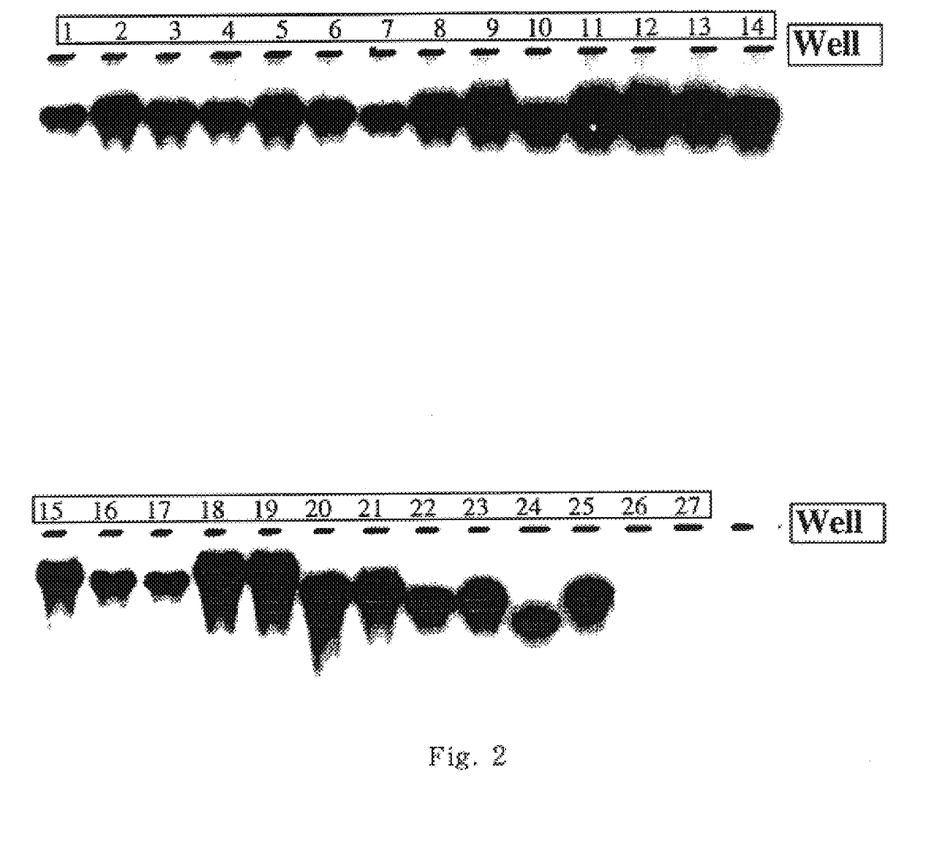
FIG. 2 schematically shows the RFLP pattern obtained by digesting chromosomal DNAs of various bacteria with EcoRV and by subjecting the resultant to Southern hybridization using S7 fragment as a probe.
Figure 3:
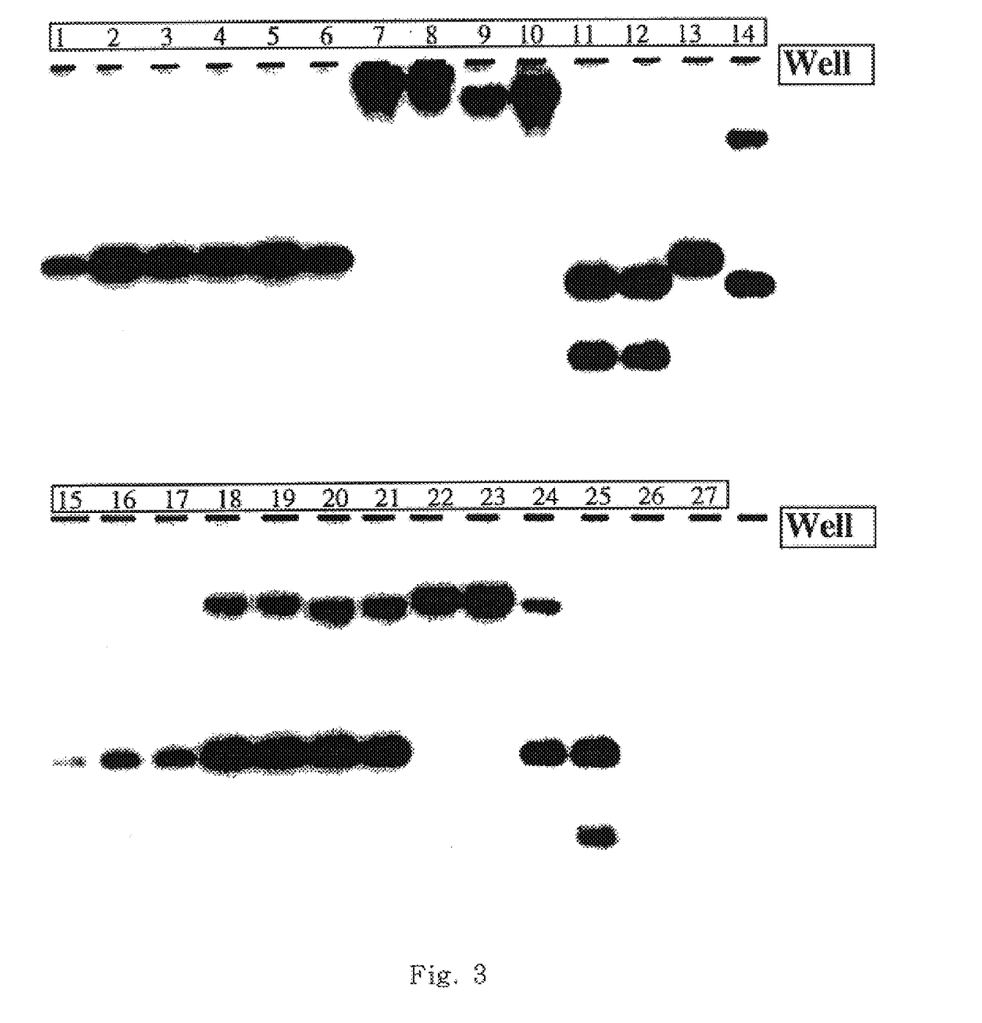
FIG. 3 schematically shows the RFLP pattern obtained by digesting chromosomal DNAs of various bacteria with SalI and by subjecting the resultant to Southern hybridization using S7 fragment as a probe.
Figure 4:
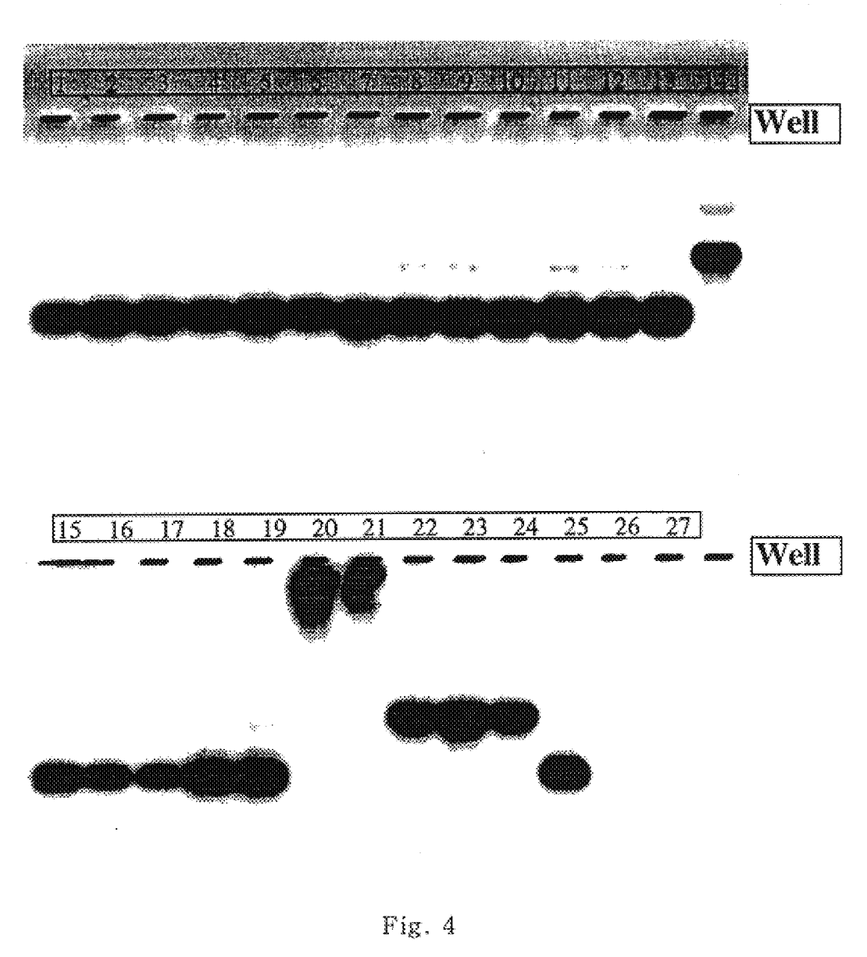
FIG. 4 schematically shows the RFLP pattern obtained by digesting chromosomal DNAs of various bacteria with PstI and by subjecting the resultant to Southern hybridization using S7 fragment as a probe.
Figure 5:
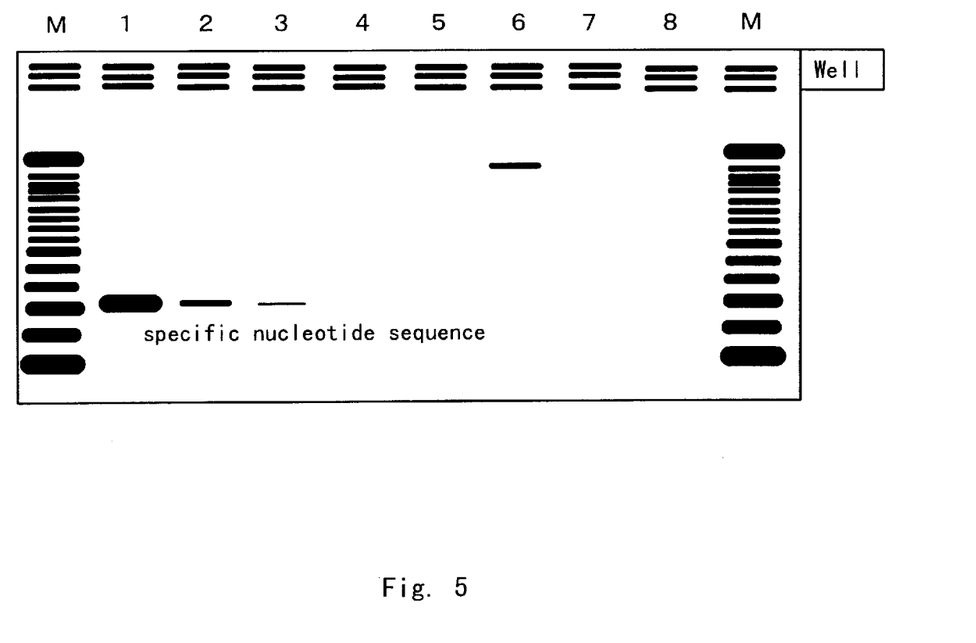

The results are shown in FIG. 5. Each lane in FIG. 5 shows the results of the samples shown in Table 3 below.

TABLE 3

| Lane No. | Sample |
|---|---|
| M | Molecular Weight Marker (100 bp ladder) |
| 1 | Suspension of JT-P482 (2.0 × 10$^4$ cfu/ml) |
| 2 | Suspension of JT-P482 (2.0 × 10$^3$ cfu/ml) |
| 3 | Suspension of JT-P482 (2.0 × 10$^2$ cfu/ml) |
| 4 | Sterilized Distilled Water |
| 5, 7, 8 | Pond Water |
| 6 | River Water |

As shown in FIG. 5, the specific DNA fragment with a size of about 300 bp was amplified only when the pathogenic *Xanthomonas campestris* pv. *poae* JT-P482 strain had been preliminarily added, and the specific DNA fragment with a size of about 300 bp was not amplified for the samples of river water, pond water and sterilized distilled water, the possibility that a pathogenic *Xanthomanas campestris* exists therein being small.

These results show that pathogenic *Xanthomonas campestris* existing in the natural environment may be quickly detected by the PCR using the primers which hybridize with regions in the S7 fragment.

What is claimed is:

1. A nucleic acid fragment consisting of SEQ ID NO:1 or the complement of this sequence or a fragment of at least 15 consecutive nucleotides of SEQ ID NO:1 which specifically hybridizes to the complement of SEQ ID NO:1.

2. The nucleic acid fragment according to claim 1, wherein the fragment which hybridizes is not less than 20 nucleotides.

3. The nucleic acid fragment according to claim 1, which is not less than 25 nucleotides in length.

4. A probe comprising the nucleic acid fragment consisting of SEQ ID NO:1 or the complement of this sequence or a fragment of at least 15 consecutive nucleotides of SEQ ID NO:1 or at least 20 consecutive nucleotides of SEQ ID NO:1 wherein the probe specifically hybridizes to SEQ ID NO:1 or the complement of SEQ ID NO:1.

5. A probe according to claim 4 comprising a detectable label attached to said nucleic acid fragment.

6. A method for detecting a *Xanthomonas campestris* pathogenic to plants belonging to the family Gramineae comprising contacting a nucleic acid sample with a nucleic acid fragment or probe consisting of SEQ ID NO:1 or the complement of this sequence or a fragment of at least 15 consecutive nucleotides of SEQ ID NO:1 which specifically hybridizes to the complement of SEQ ID NO:1 under stringent conditions and detecting a hybridization complex wherein the presence of a hybridization complex is indicative of the presence of *Xanthomonas campestris* pathogenic to plants belonging to the family Gramineae.

7. The method according to claim 6, wherein said *Xanthomonas campestris* pathogenic to plants belonging to the family Gramineae is at least one selected from the group consisting of *Xanthomonas campestris* pv. *poae*, *Xanthomonas campestris* pv. *graminis*, *Xanthomonas campestris* pv. *phlei*, *Xanthomonas campestris* pv. *arrhenatheri*, *Xanthomonas campestris* pv. *translucens*, *Xanthomonas campestris* pv. *undulosa*, and *Xanthomonas campestris* pv. *hordei*.

8. A method for detecting a *Xanthomonas campestris* pathogenic to plants belonging to the family Gramineae comprising amplifying a nucleic acid having the sequence of SEQ ID NO:1 or the complement thereof, or a fragment thereof specific to *Xanthomonas campestris* pathogenic to plants belonging to the family Gramineae, and detecting the amplified nucleic acid.

9. A method for detection or identification of a *Xanthomonas campestris* pathogenic to plants belonging to the family Gramineae which comprises digesting a sample nucleic acid with one or more restriction enzymes, separating the obtained fragments by electrophoresis, annealing the separated fragments with said probe according to claim 4, and detecting probe which hybridized with said fragments, wherein the presence of a hybridization complex is indicative of the presence of a *Xanthomonas campestris* pathogenic to plants belonging to the family of Gramineae.

10. The method according to claim 9, wherein said restriction enzyme is at least one selected from the group consisting of EcoRI, EcoRV, SalI and PstI.

11. The method according to claim 7, wherein said nucleic acid is amplified by a nucleic acid-amplification method using a pair of primers each of which consists of at least 15 consecutive nucleotides of SEQ ID NO: 1 or of the complementary chain thereof which specifically hybridizes to SEQ ID NO:1 or the complement of SEOQ ID NO:1.

12. The method according to claim 11, wherein said primers consists of 15 to 50 nucleotides.

13. The method according to claim 12, wherein said primers consists of 20 to 30 nucleotides.

14. The method according to claim 11, wherein said nucleic acid-amplification method is polymerase chain reaction method.

15. The method according to claim 13, wherein nucleic acid sequence of one of said primers is shown in SEQ ID NO: 2.

16. The method according to claim 13, wherein nucleic acid sequence of one of said primers is shown in SEQ ID NO: 3.

* * * * *

SEQUENCE LISTING

<160> NUMBER OF SEQ ID NOS: 3

<210> SEQ ID NO 1
<211> LENGTH: 1220
<212> TYPE: DNA
<213> ORGANISM: Xanthomonas campestris

<400> SEQUENCE: 1
gtcgacaggc gcttggcgca atacatggca tcgtcggcat gcgccagcaa ggcctcggcg 60
ctgtcggcat gctccggata caggctgatg ccgatgctca cgccgagccg cagcgtgtcc 120
tcaccggcga tcgcgggccg ttcgaaggct tcgatcagcg ccgtggcggt cgccgcggca 180
taggcgtcgc tgctcaatcc ggtcagcacc gccacgaact cgtcgccgcc gtaacgcgcc 240
accgtgacgt gcgcatcgac gatctcgccg atgcgttcgg cggccaggcg caggaagcgg 300
tcgccggtgg cgtgtccgag cagatcgttg atctgcttga actcgttgag atccaggaac 360
agcacggcga tgcggtggtg ttgcgcgtgc gcggtggtga tcgccagatt gagccgttcg 420
aacagcagtt cgcggttcgg caggccggtc aacgggtcgc gcttggcctg gcggttggcg 480
tcgtccagcg ccagttggta ggtgaccacc tgcgcctggg cgcgcagcgt ggtcaacacc 540
aggcgttcgt tggccgcttt caggtcggtg gcaagcccgt gcaatccatt gtccttcagt 600
gcgatcagat ccgtctgcag ccggtccagt tccagccgcg caagcagcga ctggcggcgc 660
agctgcgaca gctcgagcct ggccgcgtcg atggtgggtt gttcgggggg cgtatgcatg 720
ccggctcaac ccgtgtcgag gatgtcgtgc gtgccggcct tgcgcatcgg ccggccgccg 780
agcaggcctt cctgctgcgg cagcgccgcg ccgatgcgga tgccgtcgtc gtcgatccgg 840

```
aactcgcgca gcgcatccga atgcgcgctg gcgcggacct tgaccaccgc catcacccgg      900
cgcaagcggc tgtccacctc gatatagcgt tgcacgatga tcgcatcggt catgaacgca      960
gtgccgtagg gactgaagcg tagatcggtg tagcggtcct ccagctcgga ggtcatcagc     1020
acggtgacgc cggtcgcgcc caatgccacc accatgcgcg acagcgattc gcggaagtcc     1080
tcgcggaacg tcggcgccaa cgccagctcg aacgccgaca gcgaatcgat caccacgcgg     1140
gtggcgtcga gccgcccgat ttccgcgacc agcagcagca agatctcgtc gatcgacagg     1200
tccggcgcgc ggctgtcgac                                                 1220

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence:PRIMER

<400> SEQUENCE: 2
caatccggtc agcaccgcca cgaac                                             25

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence:PRIMER

<400> SEQUENCE: 3
acctaccaac tggcgctgga cgacg                                             25
```